United States Patent
Bosley, Jr. et al.

(10) Patent No.: US 7,766,926 B2
(45) Date of Patent: Aug. 3, 2010

(54) SLING FOR SUPPORTING TISSUE

(75) Inventors: Rodney W. Bosley, Jr., Bloomington, IN (US); Umesh H. Patel, West Lafayette, IN (US); Marvin O. Andrews, Bloomington, IN (US); LiKang Chin, Lafayette, IN (US); Frank J. Fischer, Jr., Bloomington, IN (US); Walter N. Ryan, Bloomington, IN (US); Peter L. Rosenblatt, Cambridge, MA (US); J. Stephen Jones, Shaker Heights, OH (US)

(73) Assignee: Vance Products Incorporated, Spencer, IN (US)

( * ) Notice: Subject to any disclaimer, the term of this patent is extended or adjusted under 35 U.S.C. 154(b) by 932 days.

(21) Appl. No.: 10/427,394

(22) Filed: Apr. 30, 2003

(65) Prior Publication Data
US 2004/0006353 A1   Jan. 8, 2004

Related U.S. Application Data

(60) Provisional application No. 60/376,575, filed on Apr. 30, 2002.

(51) Int. Cl.
*A61B 17/08* (2006.01)
*A61F 2/02* (2006.01)
*A61F 2/00* (2006.01)

(52) U.S. Cl. .................... 606/151; 600/30; 600/37

(58) Field of Classification Search ........... 606/151, 606/74, 76, 77, 148, 191; 600/29, 30, 37; 24/16 PB, 30.5 R, 30.5 W, 30.5 P, 20 TT, 24/17 AP, 17 A, 22, 23 R, 23 EE; 206/63.3, 206/441; 623/23.72; D8/394
See application file for complete search history.

(56) References Cited

U.S. PATENT DOCUMENTS

| 3,182,662 A |   | 5/1965 | Shirodkar |        |
|-------------|---|--------|-----------|--------|
| 3,255,501 A | * | 6/1966 | Laguerre  | 24/16 PB |
| 3,913,179 A | * | 10/1975| Rhee      | 24/16 PB |

(Continued)

FOREIGN PATENT DOCUMENTS

EP    0 248 544 B1   4/1991

(Continued)

OTHER PUBLICATIONS

Search Report dated Oct. 21, 2003, for corresponding international application No. PCT/US03/13584.

*Primary Examiner*—Julian W Woo
(74) *Attorney, Agent, or Firm*—Brinks Hofer Gilson & Lione

(57) ABSTRACT

A sling for supporting a urethra in a patient has characteristics for resisting pull-out, roll-over and a combination of both pull-out and roll-over. To facilitate resistance to pull-out, sling material has protuberances or serrations to resist movement once placed in the patient by the surgeon. Improved resistance to roll-over or roll-up is achieved by providing relief on the sling in areas potentially subjected to roll-over forces by endopelvic fascia. The sling may be used on female or male patients, and may be used in conjunction with a wider support portion to support a bladder and a urethra, rather than a urethra alone. The sling may also be used to support other tissues within a patient.

70 Claims, 8 Drawing Sheets

U.S. PATENT DOCUMENTS

| | | | |
|---|---|---|---|
| 4,037,603 A * | 7/1977 | Wendorff | 606/157 |
| 4,477,950 A * | 10/1984 | Cisek et al. | 24/30.5 P |
| 4,509,516 A | 4/1985 | Richmond | |
| 4,696,288 A * | 9/1987 | Kuzmak et al. | 128/898 |
| 5,013,292 A | 5/1991 | Lemay | |
| 5,032,508 A | 7/1991 | Naughton et al. | |
| D319,559 S * | 9/1991 | Weiss | D8/394 |
| 5,112,344 A | 5/1992 | Petros | |
| 5,250,049 A * | 10/1993 | Michael | 606/77 |
| 5,256,133 A | 10/1993 | Spitz | |
| 5,281,237 A | 1/1994 | Gimpelson | |
| 5,281,422 A | 1/1994 | Badylak et al. | |
| 5,328,077 A | 7/1994 | Lou | |
| 5,337,736 A | 8/1994 | Reddy | |
| 5,362,294 A | 11/1994 | Seitzinger | |
| 5,383,904 A | 1/1995 | Totakura et al. | |
| 5,571,117 A | 11/1996 | Ahn | |
| 5,645,568 A * | 7/1997 | Chervitz et al. | 606/228 |
| 5,647,836 A | 7/1997 | Blake, III et al. | |
| 5,711,969 A | 1/1998 | Patel et al. | |
| 5,746,763 A | 5/1998 | Benderev et al. | |
| 5,755,728 A * | 5/1998 | Maki | 606/148 |
| 5,785,640 A | 7/1998 | Kresch et al. | |
| 5,836,314 A | 11/1998 | Benderev et al. | |
| 5,840,011 A * | 11/1998 | Landgrebe et al. | 600/30 |
| 5,842,478 A | 12/1998 | Benderev et al. | |
| 5,873,904 A | 2/1999 | Ragheb et al. | |
| 5,885,619 A | 3/1999 | Patel et al. | |
| 5,899,909 A | 5/1999 | Claren et al. | |
| 5,934,283 A | 8/1999 | Willem et al. | |
| 5,955,110 A | 9/1999 | Patel et al. | |
| 5,997,554 A | 12/1999 | Thompson | |
| 5,997,575 A | 12/1999 | Whitson et al. | |
| 6,001,104 A | 12/1999 | Benderev et al. | |
| 6,030,393 A | 2/2000 | Corlew | |
| 6,039,686 A | 3/2000 | Kovac | |
| 6,042,534 A | 3/2000 | Gellman et al. | |
| 6,042,536 A | 3/2000 | Tihon et al. | |
| 6,050,937 A | 4/2000 | Benderev | |
| 6,053,935 A | 4/2000 | Brenneman et al. | |
| 6,056,688 A | 5/2000 | Benderev et al. | |
| 6,068,591 A | 5/2000 | Bruckner et al. | |
| 6,073,315 A * | 6/2000 | Rasmussen | 24/16 PB |
| 6,096,041 A | 8/2000 | Gellman et al. | |
| 6,096,070 A | 8/2000 | Ragheb et al. | |
| 6,099,547 A | 8/2000 | Gellman et al. | |
| 6,110,101 A | 8/2000 | Tihon et al. | |
| 6,179,840 B1 | 1/2001 | Bowman | |
| 6,200,336 B1 | 3/2001 | Pavenik et al. | |
| 6,206,931 B1 | 3/2001 | Cook et al. | |
| 6,221,005 B1 | 4/2001 | Bruckner et al. | |
| 6,245,082 B1 | 6/2001 | Gellman et al. | |
| 6,264,676 B1 | 7/2001 | Gellman et al. | |
| 6,273,852 B1 | 8/2001 | Lehe et al. | |
| 6,292,700 B1 | 9/2001 | Morrison et al. | |
| 6,299,604 B1 | 10/2001 | Ragheb et al. | |
| 6,302,840 B1 | 10/2001 | Benderev | |
| 6,319,272 B1 | 11/2001 | Brenneman et al. | |
| 6,322,492 B1 | 11/2001 | Kovac | |
| D451,372 S * | 12/2001 | Cedarberg, III | D8/394 |
| 6,328,686 B1 | 12/2001 | Kovac | |
| 6,334,446 B1 | 1/2002 | Beyar | |
| 6,358,284 B1 | 3/2002 | Fearnot et al. | |
| 6,475,139 B1 | 11/2002 | Miller | |
| 6,508,833 B2 | 1/2003 | Pavenik et al. | |
| 6,530,951 B1 | 3/2003 | Bates et al. | |
| 6,575,984 B2 | 6/2003 | Beyar | |
| 6,575,998 B2 | 6/2003 | Beyar | |
| 6,592,610 B2 | 7/2003 | Beyar | |
| 6,595,911 B2 | 7/2003 | LoVuolo | |
| 6,599,275 B1 | 7/2003 | Fischer, Jr. | |
| 6,612,977 B2 | 9/2003 | Staskin et al. | |
| 6,638,209 B2 | 10/2003 | Landgrebe | |
| 6,638,210 B2 | 10/2003 | Berger | |
| 6,641,524 B2 | 11/2003 | Kovac | |
| 6,652,450 B2 | 11/2003 | Neisz et al. | |
| 6,666,892 B2 * | 12/2003 | Hiles et al. | 623/23.72 |
| 6,676,674 B1 * | 1/2004 | Dudai | 606/151 |
| 6,730,064 B2 | 5/2004 | Ragheb et al. | |
| 6,774,278 B1 | 8/2004 | Ragheb et al. | |
| 6,936,052 B2 * | 8/2005 | Gellman et al. | 606/191 |
| 7,160,333 B2 * | 1/2007 | Plouhar et al. | 623/23.72 |
| 2001/0018549 A1 | 8/2001 | Scetbon | |
| 2001/0049467 A1 | 12/2001 | Lehe et al. | |
| 2001/0053916 A1 | 12/2001 | Rioux | |
| 2002/0155096 A1 | 10/2002 | Chancellor et al. | |
| 2006/0058578 A1 * | 3/2006 | Browning | 600/37 |

FOREIGN PATENT DOCUMENTS

| | | |
|---|---|---|
| EP | 0 470 308 A1 | 2/1992 |
| EP | 0 714 271 B1 | 5/1998 |
| EP | 0 598 976 B1 | 7/2000 |
| EP | 1 093 758 A1 | 4/2001 |
| EP | 1 151 722 A2 | 11/2001 |
| EP | 1 159 921 A2 | 12/2001 |
| EP | 0 854 691 B1 | 1/2002 |
| EP | 1 159 921 A3 | 1/2002 |
| EP | 0 774 240 B1 | 3/2003 |
| WO | WO 90/03766 A1 | 4/1990 |
| WO | WO 97/00047 A2 | 1/1997 |
| WO | WO 97/13465 A1 | 4/1997 |
| WO | WO 98/12971 A1 | 4/1998 |
| WO | WO 98/19606 A1 | 5/1998 |
| WO | WO 98/35606 A2 | 8/1998 |
| WO | WO 98/35632 | 8/1998 |
| WO | WO 98/35606 A3 | 12/1998 |
| WO | WO 00/09039 A1 | 2/2000 |
| WO | WO 00/66030 A1 | 11/2000 |
| WO | WO 00/74613 A1 | 12/2000 |
| WO | WO 01/17469 A1 | 3/2001 |
| WO | WO 01/26588 A2 | 4/2001 |
| WO | WO 01/45588 A2 | 6/2001 |
| WO | WO 01/45589 A1 | 6/2001 |
| WO | WO 01/47574 A1 | 7/2001 |
| WO | WO 01/52750 A1 | 7/2001 |
| WO | WO 01/56500 A2 | 8/2001 |
| WO | WO 01/93656 A2 | 12/2001 |
| WO | WO 02/19945 A2 | 3/2002 |
| WO | WO 02/26108 A2 | 4/2002 |
| WO | WO 02/28315 A2 | 4/2002 |
| WO | WO 02/058563 A1 | 8/2002 |
| WO | WO 02/065922 A1 | 8/2002 |
| WO | WO 03/020168 A1 | 3/2003 |
| WO | WO 03/028584 A2 | 4/2003 |
| WO | WO 03/030778 A1 | 4/2003 |
| WO | WO 03/034891 A2 | 5/2003 |

* cited by examiner

FIG.1
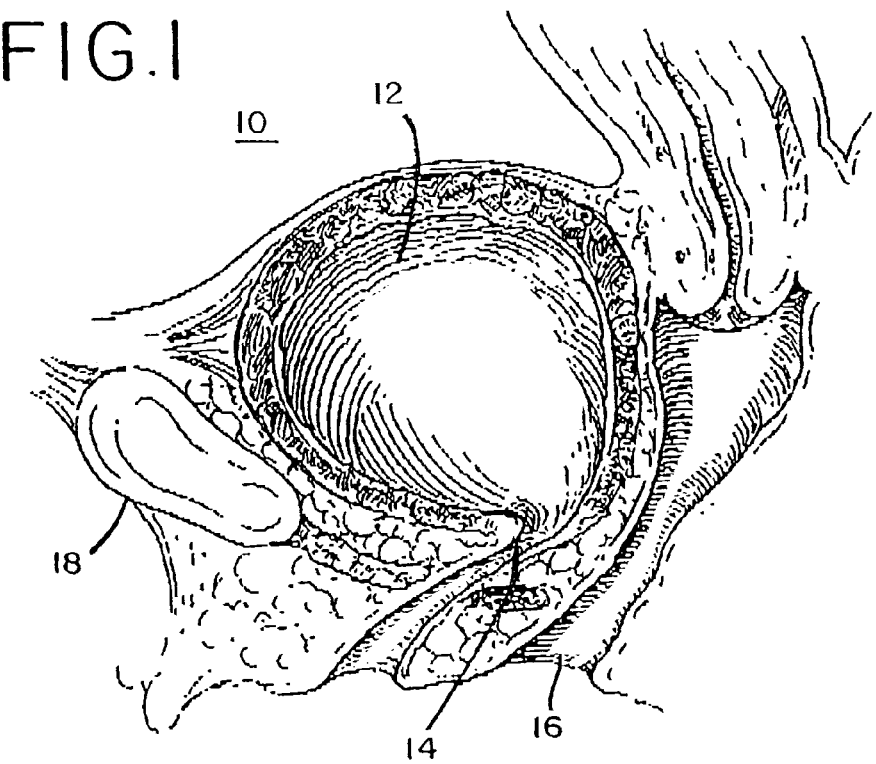
FIG.2
PRIOR ART
FIG.3
PRIOR ART
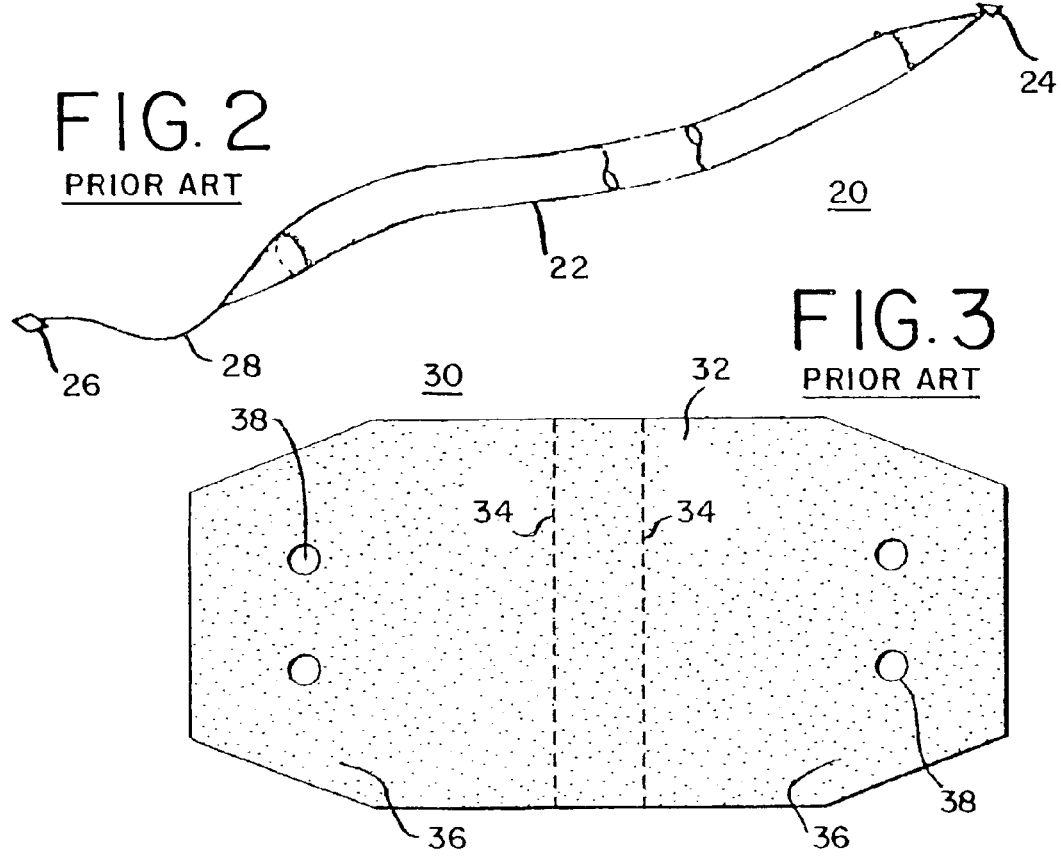

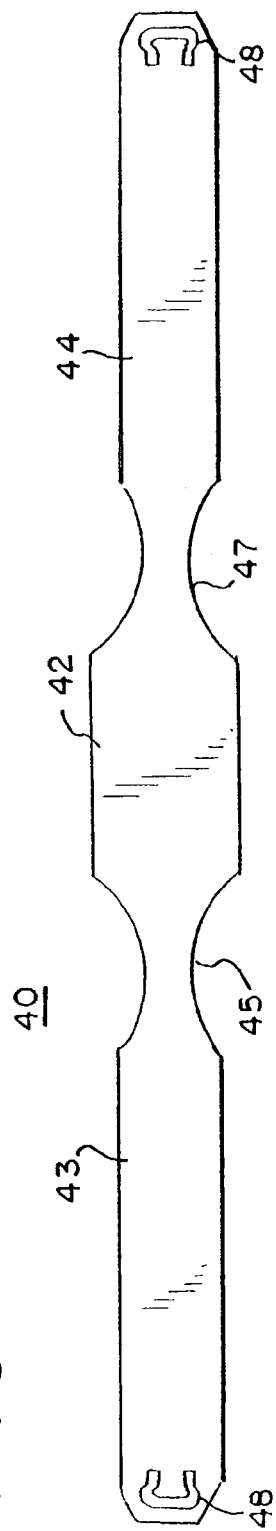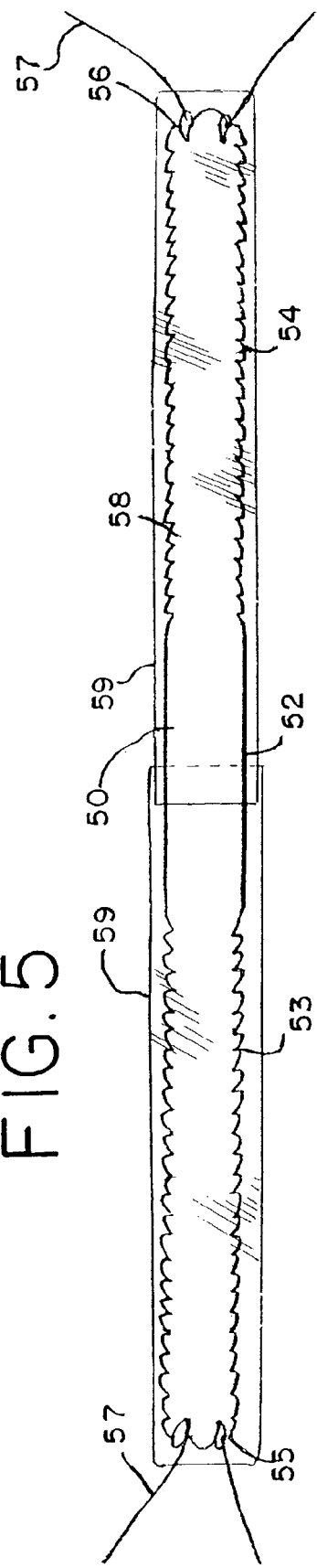
FIG. 4
FIG. 5

SLING FOR SUPPORTING TISSUE

RELATED APPLICATIONS

This application claims the benefit of the filing date under 35 U.S.C. §119(e) of Provisional U.S. Patent Application Ser. No. 60/376,575, filed on Apr. 30, 2002, which is hereby incorporated by reference in its entirety.

BACKGROUND

Urinary incontinence arising from several conditions is a common symptom in many women, especially women who had previous vaginal deliveries. Stress urinary incontinence (SUI) is the involuntary loss of urine due to increases in intra-abdominal pressure associated with laughing, lifting, coughing, or other physical activity. SUI may be caused by excessive bladder neck mobility (hypermobility) and/or intrinsic sphincter deficiency (ISD). Bladder neck hypermobility is typically the result of weak periurethral and bladder support tissue which permits the movement of the bladder neck and proximal urethra during times of increased intra-abdominal pressure. ISD is an inherent weakness of the internal urinary sphincter due to scarring or denervation which renders the internal urinary sphincter incompetent. An incompetent urinary sphincter may allow SUI in the absence of bladder neck hypermobility as urine is pushed through the incompetent sphincter with increases in intra-abdominal pressure. Some patients have both bladder neck hypermobility and ISD resulting in extreme SUI. It is important to recognize and understand that SUI is a symptom, not a disease or disorder per se.

A variety of techniques has arisen for treating the symptom of SUI. The techniques primarily involve supporting the urethra in a position where the flow of urine may be controlled by urethral compression during increases in intra-abdominal pressure. FIG. 1 illustrates the problem. Internal parts 10 of a female include a bladder 12 and a urethra 14 leading from the bladder. The urethra is a relatively small tubular organ leading from the bladder to the external portion of the body. FIG. 1 also illustrates the pubic bone 18 and the vagina 16. The urethra is shown in a relatively unsupported position, slumped to the right in FIG. 1, where the urethral sphincter may be unable to control the flow of urine in the patient.

Prior art techniques include a variety of ways to support the urethra. These ways include suturing to musculature or fascia beneath the urethra. Perhaps the most popular recent methods have involved placing a sling or hammock beneath the urethra, and supporting the hammock by anchoring it to fascia or other suitable supports, such as rectus muscle, the pubic bone, Cooper's ligament, or to subcutaneous tissue above the rectus fascia. Prior art slings are depicted in FIGS. 2 and 3. In FIG. 2, a prior art sling 20 includes a central portion 22 and means for attaching 24, 26 on the ends of the sling. These means for attaching may include tabs as shown or may include a suture 28 to allow a surgeon to draw the ends of the sling through the patient. FIG. 3 depicts another prior art sling 30. This sling has a central portion 32 with visual indicators 34 to aid the surgeon in positioning the sling under the urethra. The sling may be tapered towards the ends 36, and also has suture receiving sites 38 to resist tearing as the surgeon extends the sling through the body of the patient.

These prior art techniques have disadvantages in that they are not necessarily stable within the body of the patient. That is, once the sling is placed, it may tend to move, and thus the patient does not receive the benefit of the surgeon's precise placement of the sling for supporting the urethra and gaining the best control over incontinence. Other disadvantages lie in the design of the sling itself. Since at least the central portion of the sling has a constant width, it may be subject to rolling or bunching under the urethra. This may tend to re-form a wide band into a narrow supporting band underneath the urethra, providing less support and possibly cutting into the urethra in extreme cases.

What is needed are improved or alternative slings or hammocks for urethral support. What is needed are slings that will remain where the surgeon places them, and which will gently and reliably support the urethra and potentially other tissue structures, allowing a patient long-term relief from stress urinary incontinence.

BRIEF SUMMARY

One aspect of the invention is a sling for supporting a urethra. The sling comprises a first end portion and a second end portion, and a support portion for supporting the urethra. There is also a first transition segment connecting the first end portion to the support portion, and a second transition segment connecting the second end portion to the support portion. At least one of the transition segments provides a relief.

Another aspect of the invention is a method for supporting a urethra in a patient. The method comprises placing a sling on either side of a urethra, the sling having a support portion, and a first portion and a second end portion connected to the support portion by transition segments, wherein the transition segment defines a relief. The method also comprises creating a path on either side of the urethra, behind a pubic bone of the patient, to an abdomen of the patient. The paths are created by a method selected from the group consisting of a retrograde method and an antegrade method. The method also comprises placing the sling into the paths to anchor the sling to the patient.

Another aspect of the invention is a sling for supporting a urethra of a patient, the sling comprising a support portion, and also having a first portion and a second portion connected to the support portion. The first and second portions have serrations. Another aspect of the invention is a method for supporting a urethra in a patient. The method comprises placing a sling on either side of a urethra, the sling having a support portion, and a first portion and a second portion connected to the support portion, the first and second portions having serrations for anchoring the sling in the patient. The method also comprises creating a path on either side of the urethra, behind a pubic bone of the patient, to an abdomen of the patient. The paths are created by a method selected from the group consisting of a retrograde method and an antegrade method. The method also comprises placing the sling into the paths to anchor the sling to the patient.

Another aspect of the invention is a method for supporting tissue within a body of a patient. The method comprises placing a sling within the body, near the tissue, the sling having a support portion, and a first portion and a second portion, each connected to the support portion by a transition segment, wherein the transition segment defines a relief. The method further comprises creating a path for the first and second portions of the sling, and placing the first and second portions of the sling into the path. The method also comprises anchoring the sling. Another aspect of the invention is a method for supporting tissue within a body of a patient. The method comprises placing a sling within the body, near the tissue, the sling having a support portion, and a first portion and a second portion connected to the support portion, the first and second portions having serrations for anchoring the sling in a patient. The method further comprises creating a path for the first and second portions of the sling, and placing the first and second portions of the sling into the path. The method also comprises anchoring the sling.

There are many ways to practice the present invention, as shown in the following drawings and specification. The embodiments are not meant to limit the invention, but rather to describe and illustrate the many ways that the present invention may be used.

BRIEF DESCRIPTION OF THE DRAWINGS

FIG. 1 depicts a problem urethra requiring support.

FIG. 2 represents a prior art sling for supporting a urethra.

FIG. 3 represents another prior art sling for supporting a urethra.

FIG. 4 is an embodiment of an improved sling having transitions segments according to the present invention.

FIG. 5 is another embodiment of an improved sling having serrations according to the present invention.

DETAILED DESCRIPTION OF THE DRAWINGS AND THE PRESENTLY PREFERRED EMBODIMENTS

Figure 6:
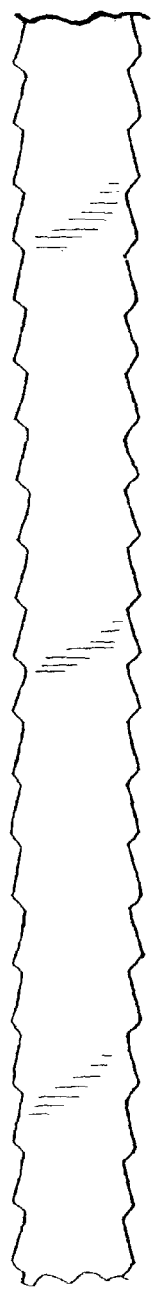
FIGS. 6-8 are further embodiments according to FIG. 5.

The present invention provides slings with adaptations for ameliorating potential causes of pull-out or roll-over of a sling, or a combination of pull-out and roll-over. In some cases, the problem of roll-over may be related to the support portion of the sling, since the primary consideration of this portion in most cases is to provide support for about 1-2 cm of the urethra, spreading the mechanical load and avoiding a stress concentration whereby the sling could damage the urethra. At least one contributor to roll-over forces and roll-over may be the endopelvic fascia, running near the urethra and roughly perpendicular to the sling. The sling may be implanted near the fascia, where the bulk and stiffness of the endopelvic fascia may interfere with a flat, planar installation of the sling by compressing the sling where the fascia pass through the sling. The sling may then be rolled or bunched into a narrow band under the urethra, depriving the urethra of broader, less stressful support.

To facilitate addressing this problem, embodiments of the present invention provide relief near the support portion of the sling. The relief features provide relief for any endopelvic fascia passing transversely to the orientation of the sling when implanted. Narrowing transitions for providing relief are preferably gently radiused so that the sling continues to provide maximum support for the urethra. The transitions are preferably narrower than the adjacent support portion and the left or right side "tail" or supporting portion of the sling. In addition to or as an alternative to narrower portions, relief may be effectively provided by modifying any material in the relief area to render it less resistant to deformation or displacement by surrounding patient tissues. For example, material in the relief area may be windowed, sliced, perforated or otherwise sufficiently weakened or otherwise modified to facilitate the passage of endopelvic fascia without curling or rolling the intermediate portion of the sling device.

Other features may be added to the sling to increase resistance to pull out, for example anchors that provide convoluted surfaces, surfaces that interfere with movement of the sling, thus increasing resistance to pullout or movement. The features or anchors may be protuberances such as barbs, whereby the sling is provided with a plurality of small anchors to prevent movement once the sling is placed into a patient. In addition, or instead of barbs or protuberances, the sling may be provided with serrations on its edges, in order to resist pullout. Other features that may help in anchoring the sling include perforations in the sling, in the support portions or in the transition regions, or both. Some of these anchoring features, especially penetrations or perforations, may also help to encourage the ingrowth of bodily tissue into the sling, thus supporting and stabilizing the sling. These features may help to stabilize the sling within the patient by increasing the surface area that opposes movement within the patient's body.

The features that improve the sling are shown in the figures. FIG. 4 depicts an improved sling 40, having a support portion 42, first (left) and second (right) portions 43, 44, and transitions 45, 47 where the support portion connects to the first and second portions. In a preferred embodiment, the sling may be about 1.5 to 2 cm wide in the support portion. Other embodiments may have a width from about 8 mm to much wider if the sling is meant to support a bladder as well as a urethra. In those embodiments, the sling may be as wide as 7 cm, and the support portion may be 4 cm long. The transitions should be smoothly radiused so as not to provide sites for initiation of tears or cracks in the material. In one embodiment, the transitions may have a radius of about 2 cm, and the narrowest portion of the sling may occur in the radiused portion, the sling being as narrow as 7-8 mm at that point. The sling may be attached to a needle or other device for implanting the sling in any convenient way. In the present embodiment, tang 48 may be molded in or machined into the sling so that the sling is easily attached to a slot or an orifice in a needle. In other embodiments, a suture may be used to attach the sling to a needle.

Another embodiment features the serrations discussed above. FIG. 5 depicts an improved sling 50 having an intermediate portion 52, first (left) and second (right) portions 53, 54, with serrations 58 on both the left and the right portions. Sling 50 also has left and right ends 55, 56, and sutures 57 attached to the left and right ends for use by a needle or other ligature carrier to implant the sling in the body of a patient. The serrated portions may be from about 10 mm wide to about 18 mm wide. The serrations may be molded into the material when it is prepared, or the serrations may be added by secondary machining or forming operations performed on the sling. The sling may be enclosed in one or more plastic sheaths 59 to ensure sterility and, in some instances, to facilitate travel of the sling through the body of the patient.

Figure 7:
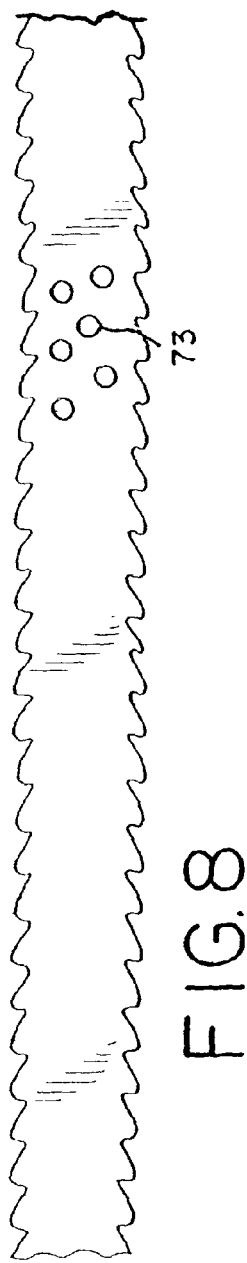
Figure 8:

Three types of serrations have been tested on a variety of materials to determine resistance to pullout. The three types of serrations are depicted in FIGS. 6-8, which depict respectively Serration I, Serration II and Serration III. Serration I may be described as the least resistive serration, with only a very gentle ridge and little difference between the "peaks" and the "troughs" of the serration. Serration II provides a much more distinct and sharp serration, almost in the form of a saw tooth, and with little relief between teeth. Serration III also provides a distinct and sharp serration, but with ample relief cut into the sling between each serration. Testing, discussed below, suggests that Serration II is the most effective of the three types, and has a significant advantage over slings with no serrations, slings with Serrations I or III, and a competitive sling that also has no serrations.

Pull-out test specimens were prepared from a variety of sling materials. Tests were conducted by inserting the sling material made of porcine small intestine submucosa (SIS) into cut surfaces of round steaks approximately 1-2 cm thick. The samples were inserted into the steak so that approximately 7 cm of each sample remained to be pulled though the steak by an Instron testing machine. The jaw of the Instron was then connected to the sling and an extension rate of about 100 mm/minute was used to pull the sling against the serrations. Maximum force was recorded as sling failure load (N). Results of the test are shown below in Table 1.

TABLE 1

| Material Type | Serration | 1.1 cm width | 2.0 cm width |
| --- | --- | --- | --- |
| 8-layer SIS, process A | None | 1.1 N | 2.33 N |
| | Serration I | 2.75 | 0.47 |
| | Serration II | 15.98 | 10.52 |
| | Serration III | 5.68 | 12.03 |
| 4-layer SIS Process A | Serration II | 4.01 | 4.1 |
| | Serration III | 2.25 | 4.84 |
| 4-layer SIS Process B | Serration II | 0.8 | 7.12 |
| | Serration III | 1.17 | 2.72 |
| 8 layer SIS process B | Serration II | 6.13 | 8.29 |
| | Serration III | 3.3 | 3.4 |
| Competitive Product | None | 2.14 | |

Subsequent testing confirmed that the serrated edges required more force to pull through, and that an 8-layer SIS laminate required at least twice as much force as a 4-layer laminate. Although serrations are clearly effective in resisting pullout, other features may desirably be added to the sling in order to make the sling even more resistant to movement within the patient's body. These features may provide a third-dimensional aspect to the otherwise flat, almost two-dimensional slings. The features may be added during normal processing of the sling material, such as when material is vacuum-processed and pressed, and a form or mold for the material contains voids or perforations for the material to fill, thus adding a desired feature.

In some embodiments, it may be beneficial to encourage the growth of bodily tissue into the sling. FIG. 7 depicts perforations 73 which have been placed into the sling in order to encourage the ingrowth of tissue. The perforations may be placed as desired, and are preferably spaced along a length of the sling for better overall support.

Processes for making multi-layer laminates from a plurality of individual layers of material are disclosed in U.S. Pat. Nos. 5,885,619 and 5,711,969, hereby incorporated by reference in their entirety. Additional teachings as to processing and layering the materials are disclosed in U.S. Pat. Nos. 5,733,337, 5,995,110, 5,993,844, 5,997,575, and 6,206,931, all of which are hereby incorporated by reference in their entirety. These patents teach the harvesting, cleansing, sterilizing and processing the submucosa from a variety of sources, including the alimentary, respiratory, urinary or genital tracts from bovine, ovine and porcine sources. Included in the processing are processes to dehydrate and compress the submucosal tissues. Processes may include vacuum drying, deadweight pressing or other pressing, lyophilizing, room temperature or heat pressing, perforating, layering, and so on. Slings made from submucosal tissues by these and other processes are meant to be used in the present invention.

The multiple-layer embodiments may contain two laminae to eight or even more laminae of collagenous material. A preferred embodiment is a four-layer or an eight-layer material made from porcine SIS, and vacuum-pressed to bind the layer in the thickness dimension. Any numbers of methods may be used to produce laminates, including the processing described above, mechanical reinforcements in the third (thickness) dimension, and the like.

Figure 9:
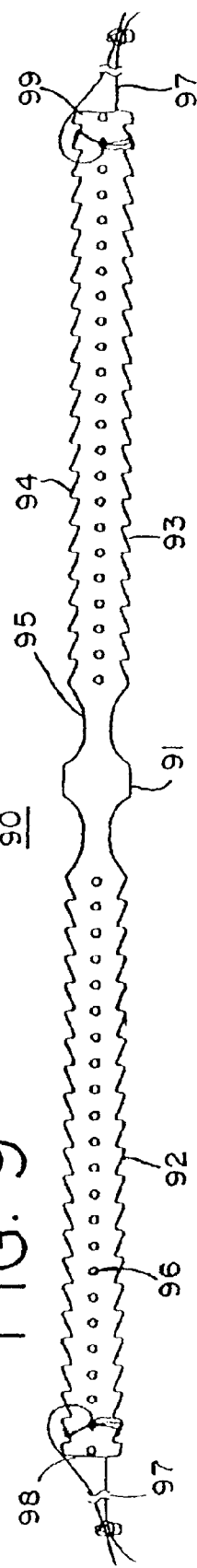
FIG. 9 is another embodiment of the present invention.

FIG. 9 depicts a sling 90 having a third-dimensional aspect added by protuberances 96 added to the surface of the material during processing. Sling 90 has a support portion 91, the support portion preferably about 2 cm wide by about 1 cm long. The support portion 91 is joined to left and right portions 92, 93 by transition or relief segments 95, wherein the narrowest portion of the sling 90 occurs in the transition segments. In a preferred embodiment, the sling may have a width of from about 6 mm to about 1.2 mm in the narrowest portions. The sling has a plurality of serrations 94 and protuberances 96 on the top surface of the sling, and may additionally or alternatively have protuberances on the bottom surface of the sling (not shown). The sling has sutures 97 on the left and right ends 98, 99 of sling 90.

As mentioned above, the protuberances may be formed during processing of the sling material by forming the material in suitable forms or molds. In one embodiment, the protuberances are in the form of buttons or short cylinders, as shown in FIG. 9, the buttons being about 1-2 mm diameter and 1-2 mm high. Other forms or shapes may be used, including regular polygons, ellipses, or other geometrical shapes. Alternatively, the protuberances may take the form of barbs or other means for retaining position in the body of a patient. Any retaining features that will help to immobilize the sling will suffice, such as protuberances, barbs, bumps, bulges, or projections, especially in the third (height) dimension.

Figure 10:
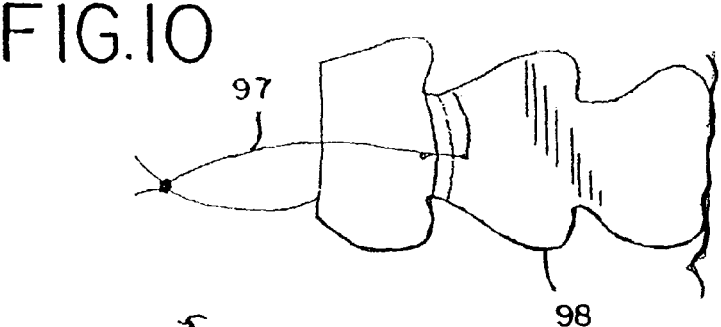
FIG. 10 is a closer view of the serrations of FIG. 7.
Figure 11:
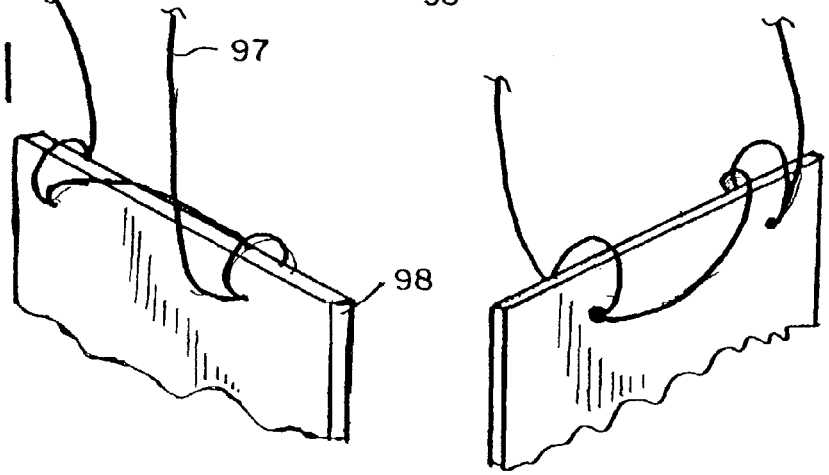
FIG. 11 is a closer view of the sutures of FIGS. 5 and 9.

FIG. 10 depicts a closer view of the left end 98 of sling 90. The sling may have serrations and may also have a suture 97 joined to the sling. In one embodiment, the sling may be about 1.5 cm wide at the wide part of each serration, and may be about 10 mm wide at the narrower part of each serration. The suture is preferably joined to the sling in such a manner that the sling does not roll over or otherwise bunch up to increase resistance when the surgeon pulls the sling through the body of the patient. The suture is therefore preferably wound through the sling with a complete loop in at least two places. A preferred embodiment of a suture mounted to a sling in shown in FIG. 11. The suture 97 is first sewn through sling end 98 and then looped at least once. The suture is then sewn through sling end 98 at a second location, followed by at least one loop. More points of attachment of the suture to the sling may be made if desired. This procedure resists rollover of the sling when it is pulled through the patient's body, and also resists tear-through when the suture is attached about 2 mm from the end of the sling.

Figure 12A:
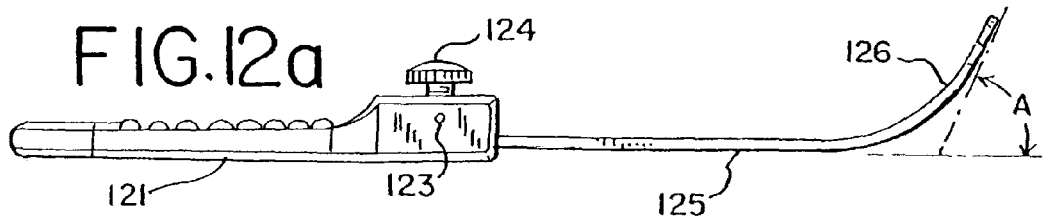
FIG. 12a is a side view of a needle and handle for implanting a sling.
Figure 12B:
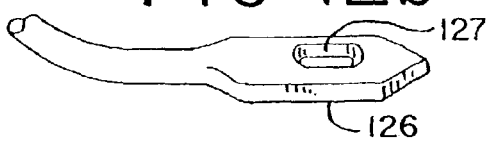
FIG. 12b is a perspective view of the needle.
Figure 13:
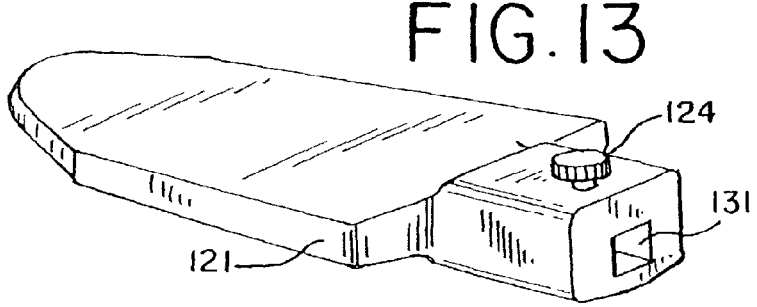
FIG. 13 is an isometric view of the handle of FIG. 12.

The sling may be used as a part of a kit furnished to a surgeon for inserting the sling into the body of a patient. The other components of such a kit are depicted in FIGS. 12a, 12b, and 13. The components may include a handle 121 for grasping by the surgeon, and a set-screw 124 for securing a needle 125 into the handle. The needle may have a proximal end 123 for securing into the handle by means of flats on the proximal end of the needle. The needle also has a distal end 126 with an aperture 127 for attaching the sling to the needle. The distal end 127 may also be flattened to more easily attach the sling to the needle. The handle 121 has an orifice 131 for accepting the proximal end of the needle. The set screw 124 is then used to snug the needle to the handle, preventing movement and rotation once the set screw is hand-tightened. The set screw may be made of metal or plastic. A needle tight and secure in the handle gives the surgeon a steady grip as the needle is used to implant the sling. The kit may also include a second needle, requiring cystoscopy to be performed only once during the implanting procedure.

The needle used may be a modified Stamey needle used as a ligature carrier, preferably having a curved portion. The curve is from about 50 degrees to about 75 degrees, shown in FIG. 12a as angle A. As mentioned above, a portion of the proximal end of the needle is flattened to fit into the handle, which has a rectangular aperture for receiving the needle. A portion of the distal end of the needle may also be flattened, and may have an aperture for attaching a suture or for directly attaching the sling. The sling may be directly attached if there is a tang or other attaching feature on the sling for inserting into the aperture in the distal end of the needle. Other ligature carriers may also be used, whether or not a suture is used to connect the sling to the needle.

An advantage of a kit which contains the needle and the sling as described above is that the operation for inserting the sling into the body of a female patient may be performed by either an antegrade or a retrograde method. This option is helpful, because some surgeons have only been trained to perform one of the above-mentioned procedures. In addition, due to previous procedures performed on a particular patient, it may be best to perform the operation by one technique rather than the other. As an example, in the antegrade technique the entire needle need not pass through the body of the patient because the sling attaches to the distal end of the needle. Only enough of the needle need pass through so that the surgeon can grasp the sling, or a suture attached to the sling.

Figure 14:
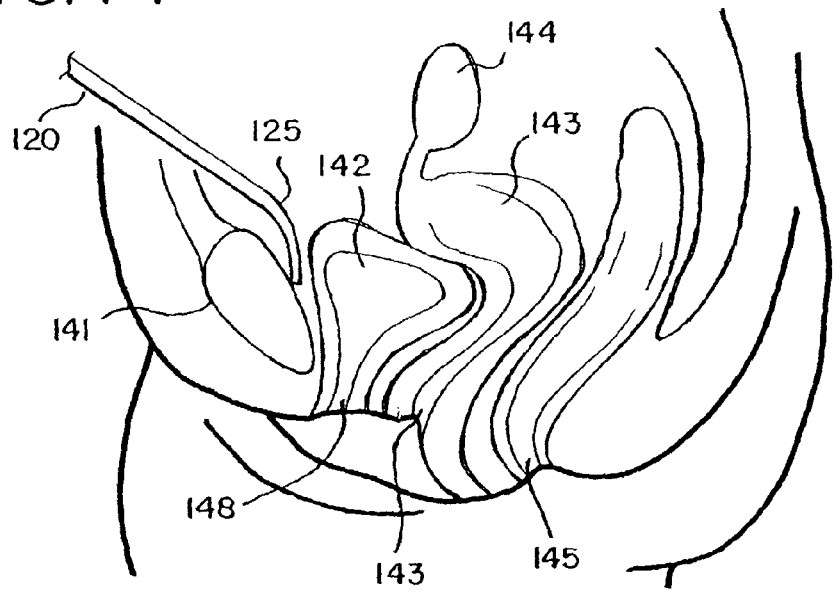
FIG. 14 is a side view of an antegrade method of implanting the sling.

An antegrade procedure is depicted in FIG. 14. FIG. 14 depicts anatomical features in the area of interest, including the pubic bone 141, bladder 142 and urethra 148, vagina 143 and uterus 144, and rectum 145. A rigid catheter guide (not shown) is deflected to the ipsilateral side just before inserting the needle, in order to minimize the risk of bladder or urethral perforation. A needle 125 is guided from a small incision on one side of the abdomen, behind the pubic bone 141, with the surgeon maintaining close contact between the distal tip of the needle and the pubic bone in order to minimize the risk of vascular injury. When the needle is delivered into the vaginal incision, the sling, or a suture attached to the sling, is placed through the aperture in the distal end of the needle, and one portion of the sling is pulled back through the tract or space developed by the needle or ligature carrier. The procedure is then repeated on the other side. The surgeon may then adjust the sling and perform a stress test by any method deemed appropriate, such as a cough test or a Q-tip test. The sling is adjusted by the left and right ends, which are then trimmed to length at the close of the procedure, preferably just under the abdominal skin.

A retrograde procedure may also be used to place the sling. In the retrograde procedure, a vaginal incision is used, and a rigid catheter guide is deflected to the ipsilateral side just before inserting the needle, in order to minimize the risk of bladder or urethral perforation. The needle or ligature carrier is inserted into a previously developed paraurethral space and advanced slightly laterally, maintaining contact with the back of the pubic bone as much as possible to minimize the risk of vascular injury. The surgeon may remove the handle from the needle and the sling, or a suture attached to the sling, is placed through the aperture in the proximal end of the needle, and one portion of the sling is pulled through the tract or space developed by the needle or ligature carrier. The procedure is then repeated on the opposite side.

Figure 15:
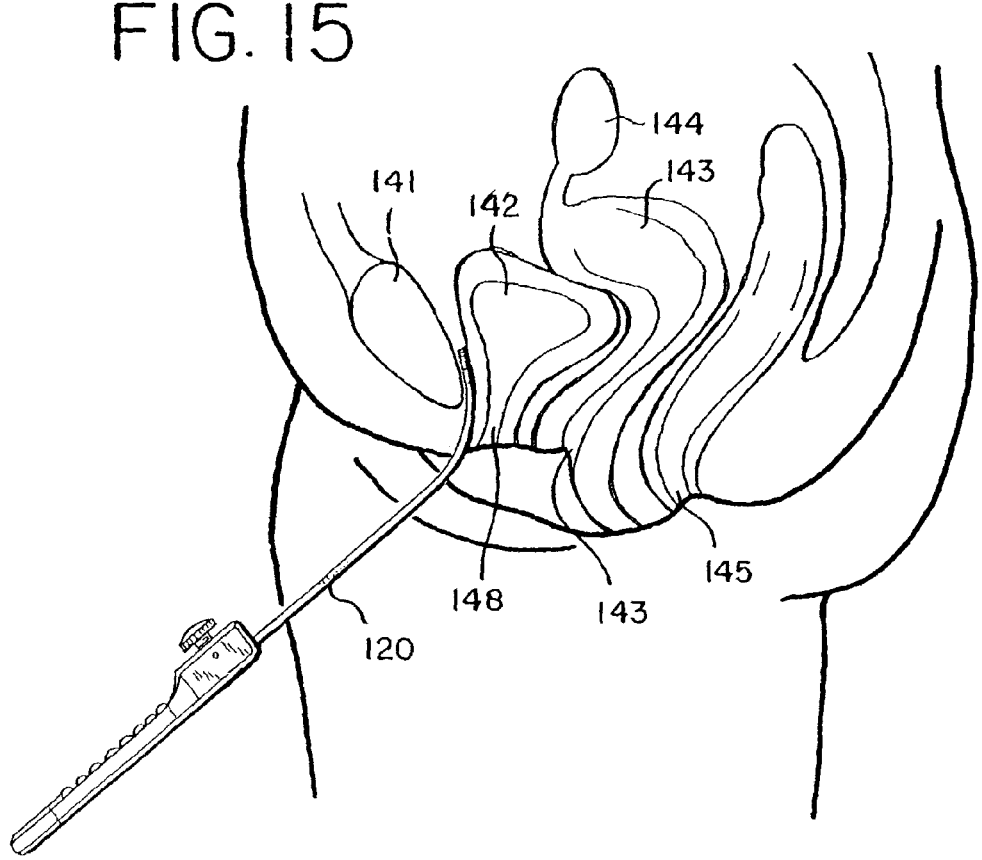
FIG. 15 is a side view of a retrograde method of implanting the sling.

FIG. 15 illustrates this technique using needle 120. Also depicted in FIG. 15 are anatomical features of concern during the procedure, including pubic bone 141, bladder 142 and urethra 148, vagina 143 and uterus 144, and rectum 145. In both the antegrade and retrograde methods, it is preferable to that the sling be in a hydrated condition before placement into the patient. This condition provides the sling with the proper amount of moisture for implantation into the patient. Thus, in cases where the sling is provided in a dehydrated state, it is preferable to rehydrate the sling for at least three to ten minutes, depending on the particular product used and the number of laminae in the product, prior to implantation in the patient.

Figure 16:
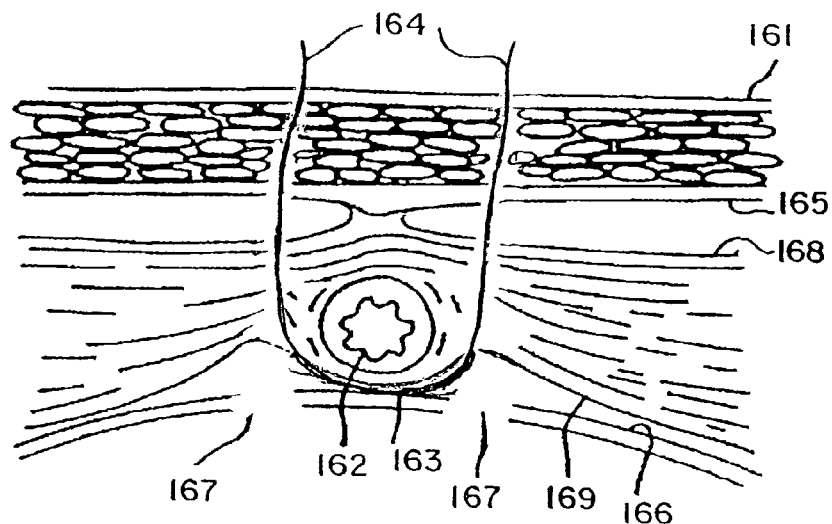
FIG. 16 is a cross sectional view of the sling in place under a urethra.

FIG. 16 is a cross-sectional view of a sling in place, supporting a urethra. Sling 163 and ends 164, shown before the ends are trimmed, extend under the abdominal skin 161 to support the urethra 162. The sling extends from just under the skin 161 through the rectus fascia 165, the rectus muscle 168 and the endopelvic fascia 169. Shown also is the vaginal mucosa 166 and the vaginal wall 167 with penetrations for placement of the sling. Portions of the endopelvic fascia may be displaced by the sling, and it is this displacement that may tend to cause rolling or bunching of the sling under the urethra. The transition or radiused portions of the sling minimize this tendency and allow stable placement of the sling.

There are other embodiments of the sling that may be used to support a urethra or other organ or tissue within a body. The embodiments discussed so far have focused on flat, relatively planar slings. It is possible to add a third dimension to the sling in one or more ways. While there may be advantages related to a flat structure, the portion that supports the urethra is actually shaped into a three-dimensional structure when it is curved under the patient's urethra. Such a three-dimensional structure may be pre-manufactured into sling devices, or sling devices may be adapted individually to suit the needs of a particular patient. The ends of the sling, whether with serrated edges or plain, may be given a third dimension by adding another plane of submucosal tissue cross-wise, as shown in FIG. 17, or by forming the ends into a corkscrew or spiral arrangement, as shown in the convoluted support portions of FIG. 18.

Figure 17:
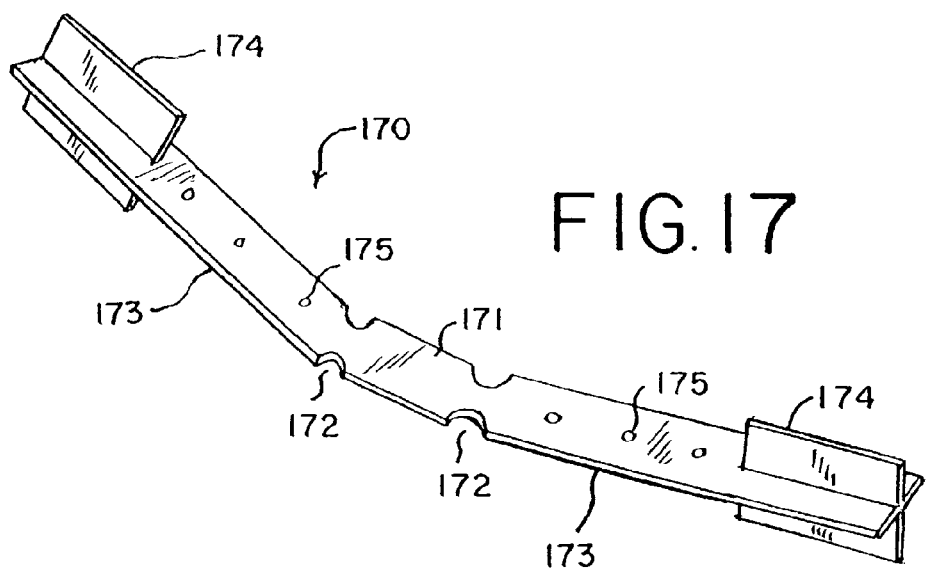
FIGS. 17-19 are additional embodiments of a sling.
Figure 19:
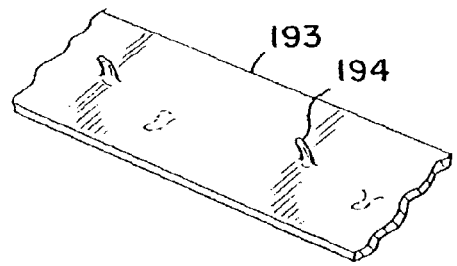

In FIG. 17, sling 170 has a support portion 171 and at least one end 173 connected to the support portion by relief 172. End 173 is generally flat and may have anchoring protuberances 175, such as small columns or cylinders or raised dots. Another anchoring piece 174 is molded or attached to end 173 at an angle for anchoring the end even more securely around other bodily parts. FIG. 19 provides a closer view of protuberances 194 in a sling end portion 193. These protuberances may be those depicted in FIGS. 9 and 17.

Figure 18:
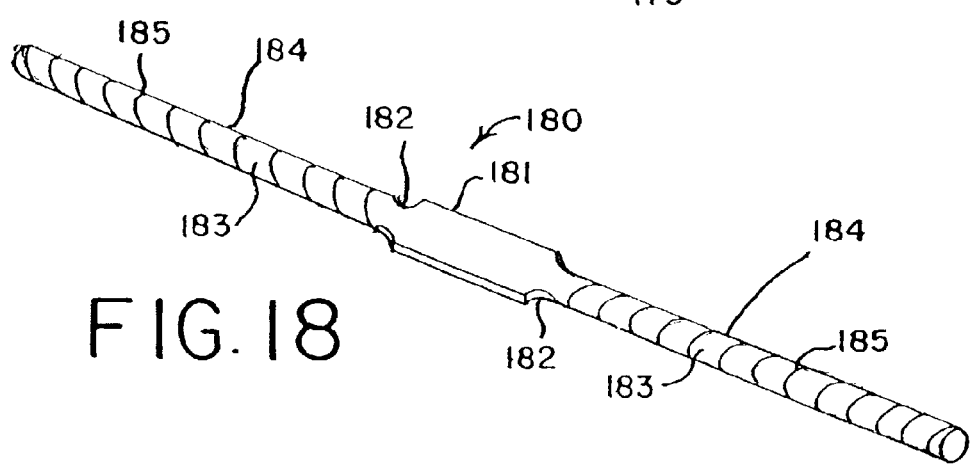

FIG. 18 depicts a sling 180 with a support portion 181 attached via transition segments 182 to ends 183. Ends 183 are formed into a convoluted spiral or helical-shaped tail for anchoring the end more securely around other bodily parts. In addition, the sling 180 may have lower portions 184 and higher portions 185 formed or molded into the sling to further assist in anchoring to a patient's body. The raised or lowered portions may be similar to threads of a screw, including a regular pitch (spacing) between raised and lowered portions 184 and 185. The pitch may be from about 0.030 inches to about 0.150 inches, preferably from about 0.060 inches to about 0.100 inches.

The embodiments of FIGS. 17-19 may be used in the same manner as that described above for antegrade or retrograde placement to support a urethra. Alternatively, if the sling is used to support a different organ or other soft tissue within the body, the three-dimensional ends of a sling may be anchored in any convenient way to a cooperating bone, ligament, or support that is available. The three dimensional aspect of the slings may help to retain them in place after a surgeon places them within the patient.

Figure 20:
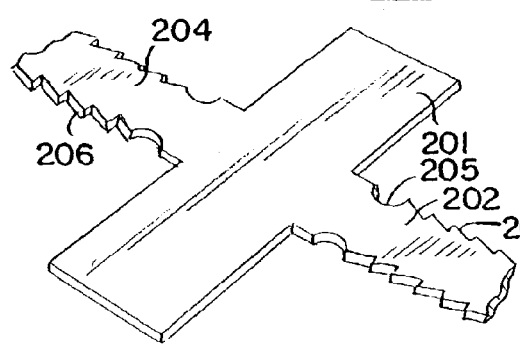
FIGS. 20 and 22 are embodiments of a sling for supporting a bladder and a urethra.
Figure 22:
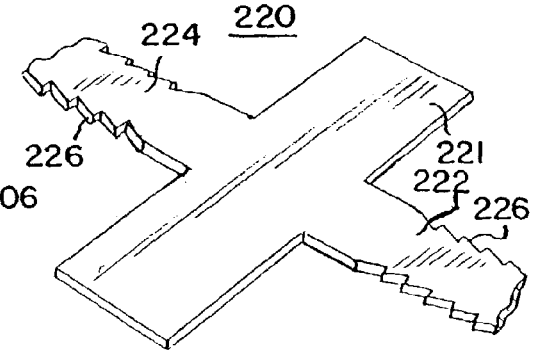

The primary use of the slings discussed so far has been to support the urethra of the patient. The slings are not limited to supporting the urethra, and may be used for other purposes. For instance, by widening the support portion of the sling, it may be used to support at least a portion of a bladder as well as a urethra. A sling for this purpose is depicted in FIGS. 20 and 22. In FIG. 20, sling 200 for supporting a urethra and at least a portion of a bladder has a support portion 201, and end portions 202, 204, connected to the support portion via transition segments 205. The end portions may also have serrations as discussed above to help prevent pullout or movement of the sling within the patient. FIG. 22 also depicts a sling 220 for supporting a urethra and at least part of a bladder. Support portion 221 is joined to first portion 222 on the right and to second portion 224 on the left. Serrations 226 help to retain the sling in place after a surgeon implants the sling.

Figure 21:
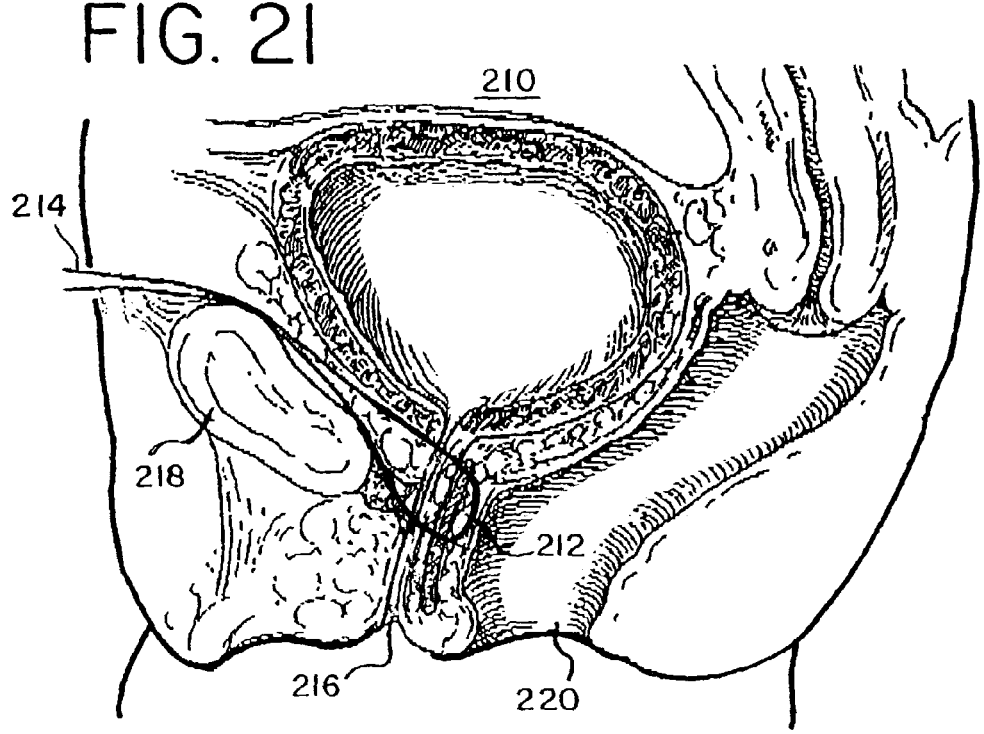
FIG. 21 depicts the desired result from implanting a sling under a urethra of a patient.

Success in the implantation of a sling may produce a result in which the urethra is supported and the user is enabled to control the flow of urine in a natural manner. The desired result of a sling implanted in patient 210 is shown in FIG. 21, in which sling 212 is held in place under the urethra 216 by sling ends 214. The ends of the sling may extend around the pubic bone 218 to just under the abdomen. If the patient also needs support for the bladder, to minimize the number of implantations and procedures, both bladder and urethral support may be provided using a device similar to the one depicted in FIG. 20.

Figure 23:
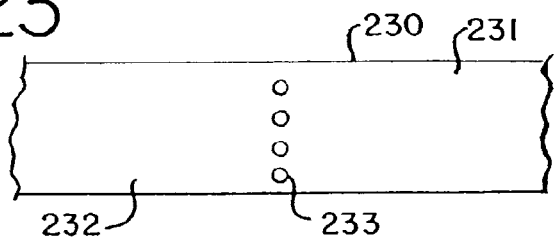
FIGS. 23-25 are top views of a sling having a support portion and a transition segment defining a relief.
Figure 24:
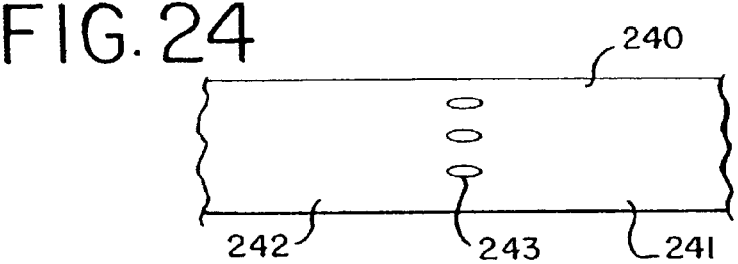
Figure 25:
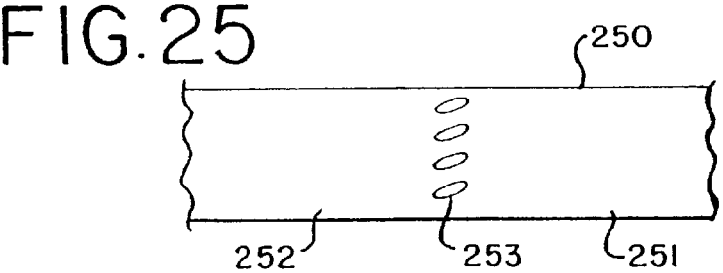

The transition segments have focused on narrowing transitions. It is also possible to provide the desired relief by transition segments in which material is perforated, sliced or otherwise weakened in specific areas to provide relief. The relief may be provided by material that has openings sliced into it, holes or windows provided, and the like. FIGS. 23-25 provide embodiments of slings in which the transition segment is so processed. FIG. 23 depicts a sling 230 having a support portion 231 and a transition segment 232 with holes 233 formed or cut into the sling material. FIG. 24 depicts a sling 240 with a support portion 241 and a transition segment with fenestrations 243 placed longitudinally in the transition segment. FIG. 25 depicts a sling 250 with a support portion 251 and a transition segment 252 with ovate penetrations 253 at about a 30° angle to the length direction of the sling. Any perforations in the areas shown, as well as other areas of the sling, including the central support portion, transitions, and support arms, may also encourage ingrowth of tissue, so that the body accepts, absorbs, supports, and integrates the sling. These techniques aid in anchoring the sling in the patient.

Figure 26:
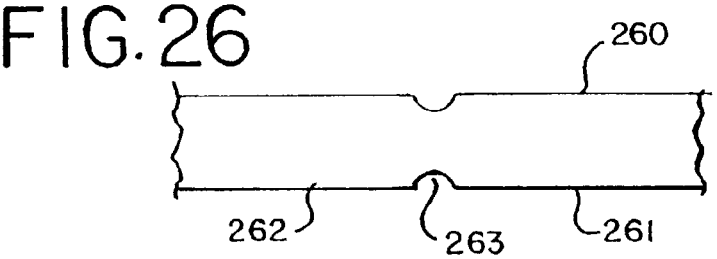
FIGS. 26-27 are cross-sectional views of a sling having a support portion and a transition segment defining a relief.
Figure 27:
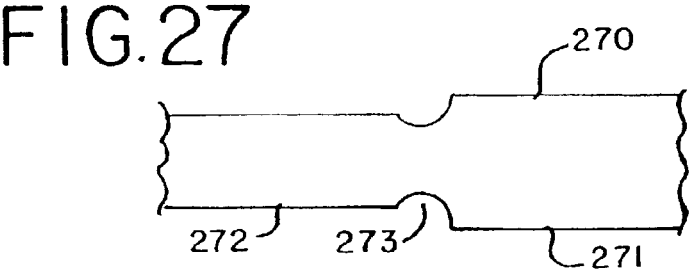

Other embodiments of a relief are shown in FIGS. 26 and 27, which show cross-sectional views of the sling. In FIG. 26, sling 260 has a support portion 261 connected to a first portion 262 via a transition segment 263. Transition segment 263 is thinner than the support segment 261 or the first portion 262.

In one example, the transition segment may be made of four layers of porcine SIS while the support and other segments may be made of eight layers of porcine SIS. In FIG. 27, a sling 270 has a support portion 271 and a first portion 272 joined by a transition segment 273. In this example, the support portion 270 may comprise 8 layers of vacuum-processed porcine SIS, and the first portion 272 may comprise 6 layers of vacuum-processed porcine SIS, while the transition segment 273 comprises 4 layers of SIS material.

The sling may be made from any suitable material. Suitable collagenous materials include, but are not limited to, purified or reconstituted collagen; bovine or other mammalian pericardium; decellularized dermis; submucosa tissue such as urinary bladder submucosa, stomach submucosa, small intestine submucosa, and uterine submucosa; serosa tissue such as bovine serosa; basement membrane tissue such as liver basement membrane; autologous, allogenic or xenogenic fascia lata; and so on. Materials which constitute a collagen-based extracellular matrix (ECM) are preferred. In general, mammalian tela submucosa tissues, which are collagen based and thus predominantly collagen, are preferred ECM materials. These tissues may be procured from the alimentary, respiratory, urinary or genital tracts of animals.

ECM materials, when used, may optionally retain growth factors or other bioactive components native to the source tissue. For example, the submucosa tissue may include one or more growth factors such as basic fibroblast growth factor (FGF-2), transforming growth factor beta (TGF-beta), epidermal growth factor (EGF), and/or platelet derived growth factor (PDGF). As well, submucosa tissue used in the invention may include other biological materials such as heparin, heparin sulfate, hyaluronic acid, fibronectin and the like.

A preferred material is small intestine submucosa (SIS) obtained from a porcine source, although the material for the sling is not limited to this material. As mentioned above, other materials useful in slings according to the present invention are disclosed in U.S. Pat. No. 6,206,931, hereby incorporated by reference. Cross-linked ECM materials are one embodiment of materials useful in the present invention, as are materials that are not cross-linked. Cross-linked materials tend to be less bioresorbable than non-cross linked materials.

A sling may also be formed from a tissue engineered product involving cell culture techniques, such as the use of stem cell technology or using smooth muscle cells with SIS material. One such technique is to seed smooth muscle cells onto SIS material or other biodegradable scaffold. Other biodegradable scaffolds, some of which are mentioned elsewhere, include polyglycolic acid (PGA), collagen, and extra-cellular matrix materials (ECM), as well as SIS. A sling may also be formed using stem cell technology. One technique is to culture stem cells in a specific medium to induce smooth muscle differentiation. Suitable media include, but are not limited to, SIS, ECM, PGA, and collagen. The new derived cells, formed from Stem cells, could be formed into the product or seeded onto the matrix material to form a sling.

Collagenous materials used for slings may be cross-linked with a chemical cross-linking agent, such as formaldehyde or glutaraldehyde. Other cross-linking agents that may be used include, but are not limited to aldehydes, sulfo-N-hydroxysuccinimide, polyepoxy compounds, and carbodiimides, including 1-ethyl-3-(3-dimethylaminopropyl) carbodiimide hydrochloride (EDC). Polyepoxy compounds may include, but are not limited to glycol diglycidyl ether, polyol polyglycidyl ether, and dicarboxylic acid diglycidyl ester. Materials for slings may also be cross-linked by radiation treatment, such as exposure to electron-beam radiation. In some instances, the strength or stiffness may in some ways be degraded by the use of electron-beam radiation. The degree of support or reinforcement necessary may determine the material used. The cross-linking lends additional strength and stiffness to materials, better enabling them to carry loads and absorb stresses. In other applications, non-cross-linked materials may suffice, and their greater flexibility and resilience may serve the patient better than a stronger, stiffer material. In addition, non-crosslinked, more bioresorbable materials are very useful in embodiments of slings useful for implantation within a human body. Slings made from any of these or other materials may also be coated with an antibacterial or an anti-inflammatory treatment to reduce infection or inflammation at the implanted sites. Slings may also be coated with an protease inhibitor to enhance tissue regeneration.

In addition to and potentially in combination with these natural materials, other natural or synthetic materials may be useful as slings or as reinforcements or additions to slings. These materials may include, but are not limited to, nylons, polyesters, polystyrene, polyethylene, polypropylene, polyacrylates, polyvinyl compounds such as polyvinyl chloride, polycarbonates, polytetrafluoroethylene, thermanox, nitrocellulose, cotton, polyglycolic acid, cat gut sutures, cellulose, gelatin, dextran, and the like. In some cases, bioresorbable materials may be indicated. Bioresorbable materials are those which ideally disappear after treatment without leaving a trace of their prior presence. Bioresorbable materials which may be used alone or in conjunction with ECM materials include, but are not limited to, biodegradable polyesters, polyorthoesters, polyglycolide-co-lactides, polyanhydrides, and polyesteramides. The slings for supporting soft tissues within the body may be made by any of these materials, or by a combination of these materials.

In addition to these materials for the slings themselves, a sling for repair of soft tissue in a human body may utilize a protective sheath, as mentioned above. The plastic sheaths desirably protect the sling and help maintain the sling in a sterile condition. In addition, the sheath may be used to help draw the sling through the body. Material for the sheath is preferably a smooth, frictionless plastic, such as polyethylene, but other plastics may also be used for a sheath, including but not limit to, polystyrene and polyvinyl chloride.

Attention has focused on urethral applications for these materials, particularly for female patients. As noted above, slings made from these materials may also be used on male patients, particularly males experiencing urinary disfunction after prostate surgery or other trauma to the urethral region. The slings made from these materials are not limited to supporting the urethra and the bladder, but may also be used for supporting a variety of soft tissues within the body. Slings made from these materials may be used for repair of a rectum or for paravaginal repairs, such as vault prolapse, cystocele, and enterocele. Abdominal walls may use these materials, as well as herniated tissues, prolapsed tissues, and perforated tissues. Suitable applications for herniated tissues may include abdominal, inguinal, diaphragmatic, epigastric, gastroesophegeal, hiatal, intermuscular, mesenteric, paraperitoneal, rectovaginal, uterine and vesical. These materials may also be used for general tissue repair in areas such as an anterior pelvic floor, bladder repair, thoracic walls, and the like.

The sling embodiments of the present invention may be made from one or more of the materials listed above, and may be used for any of the procedures listed herein. The slings are not limited to female urethral support, nor to male urethral support, but may be used in a variety of procedures to support bodily tissues. As mentioned above, multi-layer slings may be fashioned from multiple layers of materials in a variety of techniques in order to strengthen and stiffen the reinforcement.

It will be understood that no limitation of the scope of the invention is intended by the above description and drawings, which is defined by the claims below.

The invention claimed is:

1. A sling specifically configured for supporting a urethra in a patient with a hammock style arrangement, the sling comprising:
   a sterile, medically implantable sling body having a first end portion with a first length and a first width and a second end portion with a second length and a second width;
   the sling body having a support portion configured to support a urethra with the support portion disposed below the urethra to support the urethra in a hammock like orientation, with the support portion including a support length and a support width, the support portion being disposed intermediate the first and second end portions;
   a first transition segment connecting said first end portion to said support portion, and a second transition segment connecting said second end portion to said support portion, wherein the length of each of the first and second end portions is greater than the length of the support portion and the width of each of the first, second, and support portions is greater than a width of at least a portion of each of the first and second transition segments, and the first and second transition segments are configured to allow the support portion to be substantially flat to support the urethra while at least one of the first and second transition segments or the first and second end portions are compressed;
   wherein the end portions, the support portion, and the first and second transition segments are configured for passage through a needle path in soft tissue of the patient.

2. The sling of claim 1, wherein the first end portion and the second end portion are serrated.

3. The sling of claim 2, wherein the serrated portions are from about 10 mm to about 18 mm wide.

4. The sling of claim 1, wherein the transition segments are radiused from about 10 mm to about 25 mm and wherein the sling has a width of from about 6 to 12 mm in the transition segments.

5. The sling of claim 1, further comprising at least one suture about 2 mm from an end of the sling.

6. The sling of claim 1, wherein the support portion is about 2 cm wide and about 1 cm long, and wherein the transition segments are about 2 cm long.

7. The sling of claim 1, wherein the sling is made from at least one layer of vacuum-processed SIS.

8. The sling of claim 1, further comprising an anchor in the first transition segment and an anchor in the second transition segment, the anchor comprising a hole, a penetration, a serration, a protruberance, a barb, a convoluted surface, or a raised portion.

9. The sling of claim 1, wherein the support portion is about 4 cm wide and about 7 cm long, for supporting the urethra and a bladder of the patient.

10. The sling of claim 1, wherein at least one of the first end portion and the second end portion further comprises a protuberance, a button, or a tang for attaching to a needle.

11. The sling of claim 1, wherein at least one of the first end portion and the second end portion is configured as a three-dimensional anchor in the patient.

12. The sling of claim 1, further comprising a plastic sheath for the sling.

13. A combination of the sling of claim 1, at least one needle having a curved portion from about 50 degrees to about 75 degrees, and a handle, wherein the at least one needle is secured to the handle with a transverse set screw.

14. The sling of claim 1, further comprising at least one of an antibacterial treatment, an anti-inflammatory treatment, and a protease inhibitor.

15. The sling of claim 1, wherein the sling retains at least one bio-active component native to source tissue.

16. The sling of claim 15, wherein the at least one bio-active component is a growth factor.

17. The sling of claim 13, wherein the growth factor is selected from the group consisting of FGF-2, TGF-beta, EGF, and PDGF.

18. The sling of claim 1, wherein a relief is provided by material in the first and second transition segments that has been sliced, cut out, windowed or thinned.

19. The sling of claim 1, wherein the support portion and the first and second end portions each comprise a plurality of layers.

20. The sling of claim 1, wherein the support portion comprises a first plurality of layers and the first and second end portions comprise a second plurality of layers, wherein the second plurality is less than the first plurality.

21. The sling of claim 1, wherein the support portion comprises 8 layers of vacuum-processed SIS.

22. The sling of claim 21, wherein at least one of the first end portion or the second end portion comprises a 4-layer laminate of SIS.

23. The sling of claim 1, wherein at least one of the first end portion and the second end portion comprises a 4-layer laminate of SIS.

24. The sling of claim 23, wherein the 4-layer laminate of SIS is lyophilized SIS.

25. A sling for supporting a urethra of a patient, the sling comprising:
a sterile, medically-implantable sling body having a support portion configured for supporting a urethra in a hammock style orientation with a support length and a support width;
the sling body having a first portion and a second portion with respective first and second lengths and first and second widths, each of the first and second portions connected to the support portion, wherein the first portion and second portion have serrations; and
wherein the first and second lengths are greater than the support length;
wherein the first portion and the second portion are each connected to the support portion by a respective transition segment configured to allow the support portion to be substantially flat to support the urethra while at least one of the transition segments or the first and second portions are compressed, wherein the transition segments include a transition width less than the support and first and second widths, wherein at least one of the transition segments defines a relief; and
wherein said first and second portions, support portion and first and second transition segments are configured for passage through a needle path in soft tissue of the patient.

26. The sling of claim 25, wherein at least one transition segment is radiused from about 10 mm to about 25 mm and wherein the sling has a width of from about 6 to 12 mm in the transition segments.

27. The sling of claim 25, further comprising at least one suture about 2 mm from an end of the sling.

28. The sling of claim 25, wherein the support portion is about 2 cm wide and about 1 cm long, and wherein the transition segments are about 2 cm long.

29. The sling of claim 25, wherein the serrated portions are from about 10 mm to about 18 mm wide.

30. The sling of claim 25, wherein the sling is made from at least one layer of submucosa.

31. The sling of claim 25, wherein the sling is made from at least one material selected from the group consisting of synthetic materials, SIS, cross-linked extra-cellular materials, non-cross-linked extra-cellular materials, tissue-engineered materials, polyglycolic acid, collagen, and bioresorbable materials.

32. The sling of claim 25, further comprising an anchor in each said portion of the sling, the anchor selected from the group consisting of a hole, a penetration, a barb, a protuberance, and a raised portion.

33. The sling of claim 25, wherein the support portion is about 4 cm wide and about 7 cm long, for supporting the urethra and a bladder of the patient.

34. The sling of claim 25, wherein at least one of the first portion and the second portion further of a protuberance, a button, and a tang.

35. The sling of claim 25, wherein at least one of the first portion and the second portion is configured as a three-dimensional sling.

36. The sling of claim 25, further comprising a plastic sheath for the sling.

37. A combination of the sling of claim 25, at least one needle having a portion curved from about 50 degrees to about 75 degrees, and a handle, wherein the at least one handle is secured to the needle with a transverse set screw.

38. The sling of claim 25, further comprising at least one of an antibacterial treatment, an anti-inflammatory treatment, and a protease inhibitor.

39. The sling of claim 25, wherein the sling retains at least one bio-active component native to a source tissue.

40. The sling of claim 39, wherein the at least one bio-active component is a growth factor.

41. The sling of claim 40, wherein the growth factor is selected from the group consisting of FGF-2, TGF-beta, EGF, and PDGF.

42. The sling of claim 25, wherein the relief is provided by transition segments that are sliced, cut out, windowed, perforated or thinned.

43. A sling for supporting tissue within a body, the sling comprising:
a sterile, medically-implantable sling body having a support portion configured to support a urethra with a support length, the support portion configured to support the urethra in a hammock style orientation; and
a first portion and a second portion with respective first and second lengths, each of the first and second portions being connected to the support portion by a transition segment, wherein at least one of the transition segments provides an arcuate relief;
wherein the support length is less than each of the first and second lengths, and wherein the transition segments are each configured to allow the support portion to lie substantially flat while one of the transition segments or the first or second portions are compressed; and
wherein said first and second portions, support portion and first and second transition segments are configured for passage through a needle path in soft tissue of the patient.

44. The sling of claim 43, wherein the first portion and the second portion are serrated.

45. The sling of claim 44, wherein the serrations of the first and second portions are from about 10 mm to about 18 mm wide.

46. The sling of claim 43, wherein at least one of the transition segments is radiused from about 10 mm to about 25 mm and wherein the sling has a width of from about 6 to 12 mm in the transition segments.

47. The sling of claim 43, further comprising at least one suture about 2 mm from an end of the sling.

48. The sling of claim 43, wherein the sling is made from at least one layer of vacuum-processed SIS.

49. The sling of claim 43, wherein the sling is made from at least one material selected from the group consisting of synthetic materials, SIS, cross-linked extra-cellular materials, non-cross-linked extra-cellular materials, tissue-engineered materials, polyglycolic acid, collagen, and bioresorbable materials.

50. The sling of claim 43, further comprising at least one of an antiflammatory treatment, an antibacterial treatment, and a protease inhibitor.

51. The sling of claim 43, further comprising anchors in the sling, the anchors selected from the group consisting of serrations, perforations, barbs and raised portions.

52. A sling for specifically configured supporting a urethra, the sling comprising:
a sterile, medically-implantable sling body having a first end portion and a second end portion;
a sling body having a support portion intermediate the first and second end portions for supporting the urethra, the support portion specifically configured to support the urethra in a hammock style orientation;
a sling body having a first transition segment connecting said first end portion to said support portion, and a second transition segment connecting said second end portion to said support portion, wherein at least one of said transition segments provides a relief,
wherein the sling comprises a plurality of layers of extracellular matrix material and wherein the length of the support portion has more layers of the extracellular matrix material than the length of the first and second end portions when the sling is disposed in an elongate flat position; and
wherein the first and second end portions, support portion, and first and second transition segments are configured for passage through a needle path in soft tissue of the patient.

53. The sling of claim 52, wherein the transition segments are radiused from about 10 mm to about 25 mm and wherein the sling has a width of from about 6 to 12 mm in the transition segments.

54. The sling of claim 52, further comprising at least one suture about 2 mm from an end of the sling.

55. The sling of claim 52, further comprising an anchor disposed on each of the first and second end portions, the anchor comprises a serration, a perforation, a penetration, a barb, a convoluted surface, or a raised portion.

56. The sling of claim 52, further comprising an anchor disposed on each of the first and second end portions, the anchor is a serration, and each serration is from about 10 mm to about 18 mm wide.

57. The sling of claim 52, further comprising a plastic sheath for the sling.

58. The sling of claim 52, wherein the support portion comprises eight layers of SIS.

59. A sling specifically configured for supporting a urethra alone or in combination with a bladder of a patient, comprising:
a sterile, medically implantable collagenous body having a first extension, a second extension, and a support portion intermediate the first and second extensions, the support portion specifically configured for supporting a urethra in a hammock style arrangement;
wherein at least a portion of an edge of each of the first and second extensions are serrated;
the body further comprising respective transition regions disposed between the support portion and the respective first and second extension, the transition regions each having a width less than a width of each of the support and first and second extensions, the transition regions configured to allow the support portion to lie substantially flat while at least one of the transition regions or the first and second extensions are compressed;
wherein the first and second extensions, support portion, and transition regions are configured for passage through a needle path in soft tissue of the patient.

60. The sling of claim 59, wherein the collagenous body comprises an extracellular matrix material.

61. The sling of claim 60, wherein the extracellular matrix material comprises submucosa or basement membrane tissue.

62. The sling of claim 60, wherein the collagenous body comprises a plurality of layers of extracellular matrix material.

63. The sling of claim 62 wherein the support portion has a greater number of layers of extracellular matrix material than the first and second extensions.

64. The sling of claim 63, wherein the support portion has eight layers of extracellular matrix material and at least portions of the first and second extensions have four layers of extracellular matrix material.

65. The sling of claim 59, wherein the collagenous body comprises submucosa tissue.

66. The sling of claim 65, wherein the submucosa tissue is small intestinal submucosa tissue.

67. The sling of claim 66, wherein the small intestinal submucosa tissue is porcine.

68. The sling of claim 59, wherein the sling retains at least one bio-active component native to a source tissue.

69. The sling of claim 59, wherein the first extension and the second extension each has an anchor.

70. The sling of claim 69, wherein the anchor comprises one of a convoluted surface, a serration, a protruberance, a penetration, a barb, a hole or a raised portion.

* * * * *